US008563602B2

(12) United States Patent
Hitz et al.

(10) Patent No.: US 8,563,602 B2
(45) Date of Patent: Oct. 22, 2013

(54) METHOD OF IMPROVING ANIMAL TISSUE QUALITY BY SUPPLEMENTING THE ANIMAL DIET WITH OLEIC ACID AND SELECTED TOCOLS

(75) Inventors: William D. Hitz, Wilmington, DE (US); Thomas E. Sauber, Johnston, IA (US); Court Saunders, Clive, IA (US); Fred R. Wolf, Urbandale, IA (US)

(73) Assignee: E.I. du Pont de Nemours and Co., Wilmington, DE (US)

( * ) Notice: Subject to any disclaimer, the term of this patent is extended or adjusted under 35 U.S.C. 154(b) by 0 days.

(21) Appl. No.: 13/536,226

(22) Filed: Jun. 28, 2012

(65) Prior Publication Data
US 2012/0264822 A1    Oct. 18, 2012

Related U.S. Application Data

(63) Continuation of application No. 11/153,463, filed on Jun. 15, 2005, now abandoned.

(60) Provisional application No. 60/579,705, filed on Jun. 15, 2004.

(51) Int. Cl.
*A61K 31/355* (2006.01)
*A61P 21/00* (2006.01)

(52) U.S. Cl.
USPC ............................ 514/458; 426/541; 426/543

(58) Field of Classification Search
USPC ........................................................ 514/560
See application file for complete search history.

(56) References Cited

U.S. PATENT DOCUMENTS

| 5,639,870 | A | 6/1997 | Holton et al. |
| 6,239,171 | B1 | 5/2001 | Lane et al. |
| 6,242,013 | B1 | 6/2001 | Luhman et al. |
| 6,977,269 | B1 | 12/2005 | Saunders et al. |
| 2002/0151733 | A1 | 10/2002 | Ulrich et al. |
| 2002/0193617 | A1 | 12/2002 | Ulrich et al. |
| 2003/0007982 | A1 | 1/2003 | Surai et al. |
| 2003/0140372 | A1 | 7/2003 | Shen |
| 2004/0266862 | A1 | 12/2004 | Wolf et al. |

FOREIGN PATENT DOCUMENTS

EP        1 454 537       9/2004

OTHER PUBLICATIONS

Ahn, K.S., "Gamma-Tocotrienol Inhibits Nuclear Factor KB Signaling Pathway Through Inhibition of Receptor-Interacting Protein and TAK 1 Leading to Suppression of Antiapoptotic Gene Products and Potentiation of Apoptosis," *The Journal of Biological Chemistry*, 2007, pp. 809-820, vol. 282(1).

Boles et al., "Supplemental safflower oil affects the fatty acid profile, including conjugated linoleic acid, of lamb," *Journal of Animal Science* (2005), pp. 2175-2181, vol. 83(9).
Bosi et al., "Effects of dietary high-oleic acid sunflower oil, copper and vitamin E levels on the fatty acid composition and the quality of dry cured Parma ham," *Meat Science* (2000), pp. 119-126, vol. 54.
Cahoon et al., "Metabolic redisign of vitamin E biosynthesis in plants for tocotreinol production and increased antioxidant content." *Nature Biotechnology*, 2003 (published online Aug. 3, 2003), pp. 1082-1087, vol. 21(9).
Campbell, S.E. et al., "Comparative effects of RRR-alpha- and RRR-gamma-tocopherol on proliferation and apoptosis in human colon cancer cell lines", *BMC Cancer*, 2006, pp. 1-14, vol. 6.
Campbell, S.E. et al., "Gamma tocopherol upregulates peroxisome proliferator activated receptor (PPAR) gamma expression in SW 480 human colon cancer cell lines", *BMC Cancer*, 2003, pp. 1-13.
Chang et al., "Fatty acid composition and fatty acid elongase and stearoyl-CoA Desaturase Activities in Tissues of Steers Fed High Oleate Sunflower Seed," *Journal of Nutrition*, 1992, pp. 2074-2080, vol. 122.
Christen, S., et al., "Gamma-Tocopherol taps mutagenic electrophiles such as NOx and complements AlphaTocopherol: Physiological implications," *Proc. Natl. Acad. Sci.*, 1997, pp. 3217-3222, vol. 94.
Cooney, R.V., et al., "Gamma-Tocopherol detoxification of nitrogen dioxide: Superiority to Alpha-tocopherol," *Proc. Natl. Acad. Sci.*, 1993, pp. 1771-1775, vol. 90.
Descalzo et al., "Influence of pasture or grain-based diets supplemented with vitamin E on antioxidant/oxidative balance of Argentine beef," *Meat Science* (2005), pp. 35-44, vol. 70.
Gottstein et al., "Model study of different antioxidant properties of alpha-, and gamma-tocopherol in fats." *Fat Science Technology*, 1990, pp. 139-144, vol. 92(4).
Gysin, R. et al., "Gamma-Tocopherol inhibits human cancer cell cycle progression and cell proliferation by down-regulation of cyclins," *The FASEB Journal*, 2002, pp. 1952-1954, vol. 16.
Hsieh et al., "Effect of dietary monousaturated/saturated fatty acid ratio on fatty acid composition and oxidative stability of tissues in broilers," *Animal Feed Science and Technology* (2002), pp. 189-204, vol. 95.
Isnardy, B., et al., "Effects of alpha-, gamma-, and delta-Tocopherols on the Autoxidation of Purified Rapeseed Oil Triacylglycerols in a System Containing Low Oxygen," *J. Agric. Food Chem.* 2003, pp. 7775-7780, vol. 51.
Jensen et al., "Supplementation of broiler diets with all-rac-alpha- or a mixture of natural source IIRR-alpha-,gamma-,deltatocopheryl acetate. 2. Effect on the oxidative stability of raw and precooked broiler meat products." *Poultry Science*, 1995, pp. 2048-2056, vol. 74.
Jiang, Q. et al., "Gamma-Tocopherol, but not Alpha-tocopherol, decreases proinflammatory eicosanoids and inflammation damage in rats," *The FASEB Journal*, 2003, pp. 816-822, vol. 17.

(Continued)

Primary Examiner — Walter Webb

(57) ABSTRACT

A novel method for improving the meat quality of an animal is provided. The method comprises feeding the animal a diet supplemented with oleic acid and selected tocols in amounts effective to improve the meat quality. The method may be practiced on non-ruminants and ruminants.

14 Claims, No Drawings

(56) References Cited

OTHER PUBLICATIONS

Jiang, Q. et al., "Gamma-Tocopherol and its major metabolite, in contrast to alpha-tocopherol, inhibit cyclooxygenase activity in macrophages and epithelial cells", *PNAS*, 2000, pp. 11494-11499, vol. 97, No. 21.

Jiang et al., "Effects of feeding glax and two types of sunflowers seeds on fatty acid compositions of yolk lipid classes,"*Poultry Science*, 1991, pp. 2467-2475, vol. 70(12).

Lampi et al., "Effect of alpha and gamma tocopherols on thermal polymerization of purified high-oleic sunflower triaglycerols." *JOACS*, 1998, pp. 1699-1703, vol. 75(12).

Lanari, M.C., et al., "Effect of dietary tocopherols and tocotrienols on the antioxidant status and lipid stability of chicken," *Meat Science*, (2004), pp. 155-162, vol. 68.

Mikkilineni et al., "Sequence variation and genomic organization of fatty acid desaturase-2 (fad2) and fatty acid desaturase-6 (fad6) cDNAs in maize," *Theor Appl Genet*, 2003 (published online Apr. 1, 2003), pp. 1326-1332, vol. 106.

Morris, M.C. et al., "Relation of the tocopherol forms to incident Alzheimer disease and to cognitive change," *Am. J. Clin. Nutr.*, 2005; pp. 508-514, vol. 81.

Nesaretnam, K. et al., Tocotrienols Inhibit the Growth of Human Breast Cancer Cells Irrespective of Estrogen Receptor Status, *Lipids*, (1998), pp. 461-469, vol. 33, No. 5.

Ohrvall, M. et al., "Gamma, but not alpha, tocopherol levels in serum are reduced in coronary heart disease patients," *Journal of Internal Medicine*, 1996, pp. 111-117, vol. 239.

Packer, L. et al., "Symposium: Molecular Mechanisms of Protective Effects of Vitamin E in Atherosclerosis," *American Society for Nutritional Sciences*, 2001, pp. 369S-373S.

Qureshi, A. A., et al., "Dietary alpha-Tocopherol Attenuates the Impact of Gamma-Tocotrienol on Hepatic 3Hydroxy-3-Methylglutaryl Coenzyme A Reductase Activity in Chickens," *The American Institute of Nutrition*, 1996, pp. 389-394.

Rosli, W.I. Wan et al., "Vitamin E Contents of Processed Meats Blended with Palm Oils," *Journal of Food Lipds*, (2006), pp. 186-198, vol. 13.

Scheeder et al., Influence of different fats in pig feed on fatty acid composition of phospholipids and physical meat quality characteristics, *European Journal of Lipid Science and Technology*, (2000), pp. 391-401, vol. 102(6).

Suzuki, Y.J. et al., "Structural and Dynamic Membrane Properties of alpha-Tocopherol and alpha-Tocotrienol: Implication to the Molecular Mechanism of Their Antioxidant Potency," *Biochemistry*, 1993, pp. 10692-10699, vol. 32.

Tsuzuki, Wakako et al., "Intestinal Epithelial Cells Absorb gamma-Tocotrienol Faster than x-Tocopherol", *Lipids* (2007), pp. 163-170, vol. 42.

Valsta et al., "Effect of monounsaturated rapeseed oil and polyundaturated sunflower oil diet on lipoprotein levels in humans," *Arteriosclerosis, Thrombosis, and Vascular Biology*, 1992, pp. 50-57, vol. 12.

Van Eanennaam et al., "Engineering Vitamin E Content: From Arabidopsis Mutan Soy Oil," *The Plant Cell*, 2003; pp. 3007-3019, vol. 15.

Warner et al., "Compositions of Sunflower, Mid-Oleic Sunflower, and High Oleic Sunflower Oils," *Proceedings Sunflower Research Workshop*, 2003.

Yurttas et al., Abstrace 92A-9, "Expoloring the antioxidant activity of tocohienols in meat systems," IFT Food Expo, Jul. 13-16, 2003, McCormick Place, Chicago, IL.

Zanardi et al., "Oxidative Stability and Dietary Treatment with Vitamin E, Oleic Acid and Copper of Fresh and Cooked Pork Chops," *Meat Science* (1998), pp. 309-320, vol. 49(3).

Zhou, C. et al., "Tocotrienols Activate the Steroid and Xenobiotic Receptor, SXR, and Selectively Regulate Expression of its Target Genes," *Drug Metabolism and Disposition* (DMD), 2004, pp. 1075-1082, vol. 32, No. 10.

E.I. DuPont de Nemours & Company, Notice of Allowance from European Patent Application No. 05 761 518.9 filed Mar. 7, 2008, 4 pages.

E.I. DuPont de Nemours & Company, Allowed Claims in the European Patent Application 05 761 518.9, 3 pages, date: Mar. 28, 2007.

METHOD OF IMPROVING ANIMAL TISSUE QUALITY BY SUPPLEMENTING THE ANIMAL DIET WITH OLEIC ACID AND SELECTED TOCOLS

CROSS-REFERENCE TO RELATED APPLICATIONS

This application is a continuation of U.S. application Ser. No. 11/153,463, filed Jun. 15, 2005, which claims the benefit of U.S. Provisional Application No. 60/579,705, filed Jun. 15, 2004, the contents of which are hereby incorporated in their entirety by reference herein.

FIELD OF THE INVENTION

This patent relates to a method of improving animal tissue quality. More specifically, this patent relates to a method of improving animal tissue quality by administering to the animal effective amounts of oleic acid and selected tocols in combination.

BACKGROUND OF THE INVENTION

The oxidative stability of meat products is of importance with respect to retail shelf life. Oxidative color deterioration in fresh beef, for example, has been estimated to cost U.S. retailers over $1 billion per year due to discounted and discarded product.

At present, refrigeration and packaging are the primary deterrents to oxidative deterioration. Several technologies are utilized, including modified atmospheric packaging (MAP), which involves removing the air from a gas impermeable meat package and replacing the air with various gas mixtures (e.g. 8:2 oxygen:carbon dioxide). MAP can improve meat color (i.e., oxymyoglobin stability), but at the same time gas mixtures that contain high oxygen concentrations negatively affect lipid (and hence flavor) stability owing to the relatively high concentration of oxygen in the package.

Research indicates that supplementation of the animal diet with vitamin E in the form of alpha-tocopherol acetate (ATA) at supranutritional levels is an effective means for improving meat quality (Morrissey, P. A., Buckley, D. J. and Galvin, K. 2000). *Vitamin E and the oxidative stability of pork and poultry*, in *Antioxidants in Muscle Foods*, E. A. Decker, C. Faustman and C. J. Lopez-Bote (eds.), pp. 263-287. John Wiley & Sons, Inc.). In addition to improved color, supplementation of the animal diet with ATA results in improved stability of membrane-bound lipids, maintenance of cell membrane integrity, and reduced purge (Monahan, F. J., et al., Food Chem. 1993). ATA does not, however, provide consistent results, and must be incorporated into the animal diet over a fairly long period of time, depending on the dietary concentration. Supranutritional levels of ATA are sometimes used commercially in cattle feed, though not yet for poultry or swine, owing to an inadequate cost-to-benefit ratio.

Therefore, there is a need in the art for cost-effective methods of providing improvements to the tissue quality of an animal with respect to meat quality.

However, to the inventors' knowledge, no one heretofore has studied the effects on meat quality of supplementing the animal feed with a combination of oleic acid and tocotrienols or oleic acid and gamma-tocopherol. Applicants have now discovered that supplementation of the animal diet with oleic acid and either tocotrienols or gamma-tocopherol results in improvements to oxidative stability greater than that observed from oleic acid, tocotrienols or gamma-tocopherol alone.

DETAILED DESCRIPTION OF THE INVENTION

The present invention is a novel method for improving the tissue quality of an animal, the method comprising feeding the animal a diet including oleic acid (OA) and selected tocols (ST) in amounts effective to improve the tissue quality. The operable dietary range is at least about 3% by weight oil, whose fatty acid fraction consists of at least 50% OA, and from about 50 ppm to about 500 ppm ST. The preferred dietary range is from about 3% to 10% by weight oil, whose fatty acid fraction is at least 80% is OA, and from about 150 ppm to about 300 ppm ST. The optimum diet should contain about 5% to 10% by weight total dietary oil, whose fatty acid fraction is at least 80% is OA, and about 225 ppm ST, fed to the animal for at least 30 days for swine, at least 50 days for cattle and for at least 20 days for poultry.

"Selected tocols" (ST) as used herein refers to one or more of the tocotrienols (TT), gamma-tocopherol (GT), or a mixture of at least one tocotrienol and gamma-tocopherol. The selected tocols may contain other components, including other tocopherols.

"Tocotrienols" as used herein refers to any individual tocotrienol or any mixture of two or more tocotrienols. The mixture may contain other components, including tocopherols.

Tocotrienols, like their chemical cousins the tocopherols, are fat soluble nutrients, but are less widely distributed in nature. The four known tocotrienols are alpha-, beta-, gamma- and delta-tocotrienol. Tocotrienols occur naturally in cereal grains (including barley, corn and rice) and certain vegetable oils such as, but not limited to, palm and grapeseed oil.

The selected tocols can be one of the tocotrienols, gamma tocopherol, or a mixture of tocotrienols and/or gamma tocopherol. The tocotrienols may be a mixture of two or more of the four known tocotrienols or a single tocotrienol, such as, but not limited to, gamma-tocotrienol. The tocotrienols may be in the form of a distillate obtained from seed processing or genetically modified oilseed or grain having an increased tocotrienol concentration. The genetically modified oilseed or grain can be modified by transgenic methods well known in the art (see for example: Crossway et al. (1986) Biotechniques 4: 320-334), electroporation (Riggs et al. (1986) Proc. Natl. Acad. Sci. USA 83: 5602-5606, Agrobacterium-mediated transformation (Townsend et al., U.S. Pat. No. 5,563, 055; Zhao et al., U.S. Pat. No. 5,981,840), direct gene transfer (Paszkowski et al. (1984) EMBO J. 3: 2717-2722), and ballistic particle acceleration (see, for example, Sanford et al., U.S. Pat. No. 4,945,050; Tomes et al., U.S. Pat. No. 5,879, 918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6: 923-926); and Led transformation (WO 00/28058). Also see Weissinger et al. (1988) Ann. Rev. Genet. 22: 421-477; Sanford et al. (1987) Particulate Science and Technology 5: 27-37 (onion); Christou et al. (1988) Plant Physiol. 87: 671-674 (soybean); McCabe et al. (1988) Bio/Technology 6: 923-926 (soybean); Finer and McMullen (1991) In Vitro Cell Dev. Biol. 27P: 175-182 (soybean); Singh et al. (1998) Theor. Appl. Genet. 96: 319-324 (soybean); Datta et al. (1990) Biotechnology 8: 736-740

(rice); Klein et al. (1988) Proc. Natl. Acad. Sci. USA 85: 4305-4309 (maize); Klein et al. (1988) Biotechnology 6: 559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91: 440-444 (maize); Fromm et al. (1990) Biotechnology 8: 833-839 (maize); Hooykaas-Van Slogteren et al. (1984) Nature (London) 311: 763-764; Bowen et al., U.S. Pat. No. 5,736,369 (cereals); Bytebier et al. (1987) Proc. Natl. Acad. Sci. USA 84: 5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) Plant Cell Reports 9: 415-418 and Kaeppler et al. (1992) Theor. Appl. Genet. 84: 560-566 (whisker-mediated transformation); D'Halluin et al. (1992) Plant Cell 4: 1495-1505 (electroporation); Li et al. (1993) Plant Cell Reports 12: 250-255 and Christou and Ford (1995) Annals of Botany 75: 407-413 (rice); Osjoda et al. (1996) Nature Biotechnology 14: 745-750 (maize via Agrobacterium tumefaciens). The genetically modified oilseed or grain can also be modified by means of naturally occurring or induced mutations (see, for example, Bensen et al. (1995) Plant Cell 7:75-84; Mena et al. (1996) Science 274:1537-1540; U.S. Pat. No. 5,962,764; Ohshima, et al. (1998) Virology 243:472-481; Okubara et al. (1994) Genetics 137:867-874; Quesada et al. (2000) Genetics 154:421-436 and McCallum et al. (2000) Nat. Biotechnol. 18:455-457). The gamma-tocopherol can be in the form of a distillate obtained from seed processing, a genetically modified crop, or any other suitable form.

The oleic acid may be in the form of vegetable oil having an elevated level of oleic acid, including, but not limited to: high-oleic corn, sunflower, soybean, cotton, cocoa, peanut, safflower, or canola oil. The oleic acid may also be fed in the form of these oilseed or grain crops arising from plants genetically modified to express a high-oleic trait. The genetically modified oilseed or grain may be modified by transgenic methods well known in the art, or as naturally occurring or induced mutations. A "high oleic" trait is a trait wherein the oilseed or grain exhibits a greater than wild-type level of oleic fatty acid. See WO Pub. 94/11516, WO Pub. 90/10380, WO Pub. 91/11906, and U.S. Pat. No. 4,627,192 herein incorporated in their entirety by reference.

A fat or oil source with an iodine value comparable to or lower than a high-oleic vegetable oil source such as, but not limited to, high-oleic sunflower oil may also be utilized.

In one embodiment, the oleic acid and the selected tocols are added to the feed in the form of a corn grain arising on ears of corn plants that express the FAD-2 and HGGT genes for the high-oleic acid and high-tocotrienol phenotypes respectively. See U.S. Pub. 0034886, and U.S. Pat. No. 6,372,965 herein incorporated in their entirety by reference.

As used herein "elevated levels" means levels of oleic acid or selected tocols expressing in genetically modified plants at levels higher than wild-type plants.

The animal may be a non-ruminant, such as, but not limited to, swine, poultry or fish, or a ruminant, such as, but not limited to, cattle or lamb.

In the examples that follow, meat tissue quality is measured using a number of parameters, including color score, percent discolorization and oxidative stability (TBARS level). The method has been proven effective with swine and cattle, and would be expected to be effective with other non-ruminants and ruminants. The improved tissue may comprise any animal tissue, and includes muscle meat, organs, milk and eggs.

The feed test trials were conducted on swine (a non-ruminant) and cattle (a ruminant). It is expected that the invention will also be effective with other non-ruminants such as, but not limited to, poultry and fish and with other ruminants such as, but not limited to, lamb and bison.

The present invention is further defined by the following examples. The examples, while indicating particular embodiments of the invention, are given by way of illustration only. From the discussion contained herein and the examples themselves, one skilled in the art can ascertain the essential characteristics of the invention and, without departing from the scope thereof, make changes and modifications to the invention to adapt it to various situations and conditions.

The following abbreviations are used throughout the examples: control (CO), oleic acid (OA), high-oleic (HO), selected tocols (ST), tocotrienols (TT), gamma-tocopherol (GT) and thiobarbituric acid reactive substances (TBARS). The oleic acid additive amounts are expressed as a percentage of the total fatty acid fraction within the oil. The tocotrienol additive amounts are expressed as weight parts additive per million weight parts feed (ppm).

EXAMPLE 1

2003 Swine Feed Test

Demonstration that Supplementation of Swine Diet with Oleic Acid and Tocotrienols Results in Improved Tissue Quality Parameters Applicants assessed the effects of supplementing the animal diet with oleic acid and tocotrienol on pork meat quality in an experiment in which data from pigs fed one of four dietary treatments were compared. Seventy-two barrows (approximately 20 kg) were randomly placed in pens with water and feed provided ad libitum at the Pioneer Livestock Nutrition Center (PLNC) in Polk City, Iowa. Ad libitum swine feeding continued for 49 days (through Mar. 4, 2003) until the average weight reached 32 kg. A uniform group of 64 pigs was selected, and the pigs were randomly assigned to each of four treatments with 16 experimental units (individually housed pigs) per dietary treatment.

On Apr. 22, 2003 (Day 1 of the feed test) the feeders were emptied and the dietary treatments were commenced and continued until Jul. 14, 2003 (Day 83). Dietary treatments consisted of two levels of oleic acid (normal and high) with or without tocotrienol (0 or 225 ppm), as summarized below:

TABLE 1

DIETARY TREATMENTS

| Treatment | Total Dietary Oil Content, % | Oleic acid content | | Tocotrienol, ppm[1] |
|---|---|---|---|---|
| | | Corn oil | Sunflower oil | |
| Normal oleic acid (CO) | 5.5 | 29.6% | | 0 |
| Normal oleic acid + TT (TT) | 5.5 | 29.6% | | 225 |
| High oleic acid (HO) | 5.5 | | 80.2% | 0 |
| High oleic acid + TT (HO + TT) | 5.5 | | 80.2% | 225 |

[1]The 225 ppm dietary treatment included about 75 ppm alpha-tocopherol, for a total tocol concentration of about 300 ppm.

In the normal or control (CO) diet, the total dietary content of oil was 5.5 wt % of the feed. The oil was a typical corn oil having an oleic acid content of 29.6 wt % of the fatty acid fraction. In the high-oleic acid (HO) diet, the total dietary content of oil was still 5.5 wt %, but the oil was high-oleic sunflower oil with an oleic acid content of 80.2 wt % of the fatty acid fraction. The high oleic sunflower oil was purchased from Cargill, Inc. All four experimental diets were formulated with soybean meal and corn flaking grits. The latter, being largely devoid of oil, were used in conjunction with the corn and high-oleic vegetable oils to achieve the desired dietary fatty acid content.

The tocotrienol used to supplement the (TT) and the (HO+TT) diets was obtained commercially from Fuji Chemical Industries (U.S.A.) Inc. of Robbinsville, N.J., and contained 7.5% alpha-, 12.3% gamma- and 3.0% delta-tocotrienol (a total tocotrienol content of 22.8%), as well as 7.2% alpha-tocopherol.

The pigs were weighed every 14 days after treatment initiation. When the average weight of the treatment group reached >114 kg (Jul. 7, 2003), 32 pigs representing the heaviest representatives for each treatment (8 from each pen) were transported to the University of Missouri (Columbia) abattoir. The remaining pigs were weighed and transported to the University of Missouri Meat Lab.

The pigs were slaughtered at an average weight of 120 kg on Jul. 21, 2003 and various carcass measurements were taken. Following a 24 hour chill period, the carcasses were transferred to the University of Missouri processing lab, where weight yields were recorded and meat tissue was evaluated.

The right pork carcass side was fabricated into primal and sub-primal cuts and the bellies were evaluated for thickness, firmness and fatty acid profile. Table 2 summarizes the effect of feed supplementation on belly thickness and firmness (flex):

TABLE 2

EFFECT OF FEED SUPPLEMENTS ON
BELLY THICKNESS AND FLEX[1,2]

| Item | Control (Corn oil) CO | Corn oil + 225 ppm TT | High oleic sunflower oil HO | High oleic sunflower oil + 225 ppm TT HO + TT |
|---|---|---|---|---|
| Belly thickness, mm | 35.6 | 35.4 | 35.1 | 36.1 |
| Vertical flex | 19.8 | 19.8 | 19.1 | 18.3 |
| Lateral flex | 8.6$^a$ | 8.7$^a$ | 10.7$^b$ | 11.3$^b$ |

[1]Treatment means in same row with unlike superscripts differ (P < or = 0.05).
[2]Lower vertical, or higher lateral, flex scores indicate a firmer belly.

As indicated in Table 2, belly thickness and vertical flex measurements were not significantly affected by dietary treatment. However, lateral flex scores were significantly higher (P< or =0.05), indicating greater firmness, for bellies from pigs fed the high-oleic acid (HO) diet and the high-oleic acid and tocotrienols (HO+TT) diet.

In order to isolate the effects of oleic acid level and tocotrienol addition on belly thickness, vertical flex and lateral flex, the data in Table 2 was recalculated in terms of oleic acid level and tocotrienol addition. The results are given in Table 3 below:

TABLE 3

EFFECT OF OLEIC ACID LEVEL AND DIETARY
TOCOTRIENOL SUPPLEMENTATION ON BELLY
THICKNESS AND FLEX[1,2]

| Item | Oleic Acid Level | | Tocotrienol Addition | |
|---|---|---|---|---|
| | Normal | High | 0 ppm | 225 ppm |
| Belly thickness, mm | 35.5 | 35.6 | 35.3 | 35.8 |
| Vertical flex | 19.8 | 18.7 | 19.4 | 19.1 |
| Lateral flex | 8.7$^a$ | 11.0$^b$ | 9.7 | 10.0 |

[1]Treatment means in same Oleic Acid Level row with unlike superscripts differ (P < or = 0.05).
[2]Lower vertical, or higher lateral, flex scores indicate a firmer belly.

As indicated in Table 3, the lateral flex score improvement shown in Table 2 in the (HO+TT) diet compared to the normal (CO) diet was mostly due to the increased level of oleic acid in the feed. Tocotrienol addition did not significantly affect lateral flex score.

The fatty acid composition and iodine values in the pork belly adipose tissue was measured. A summary of the results is presented in Table 4 below:

TABLE 4

EFFECT OF DIETARY TREATMENTS ON BELLY ADIPOSE
TISSUE FATTY ACID COMPOSITION[1]

| | Control (Corn oil) CO | Corn oil + 225 ppm TT | High oleic sunflower oil HO | High oleic sunflower oil + 225 ppm TT HO + TT |
|---|---|---|---|---|
| Monounsaturated Fatty Acid (MUFA) | 42.4$^b$ | 41.8$^b$ | 55.1$^a$ | 56.0$^a$ |
| Polyunsaturated Fatty Acids (PUFA) | 20.0$^a$ | 21.0$^a$ | 9.8$^b$ | 9.6$^b$ |
| Iodine Value (IV) | 69.4$^a$ | 70.6$^a$ | 63.5$^b$ | 64.0$^b$ |

[1]Treatment means in same row with unlike superscripts differ (P < or = 0.05).

As shown in Table 4, monounsaturated fatty acid (MUFA) concentration trended higher and polyunsaturated fatty acid (PUFA) concentration trended lower in the belly adipose tissue from pigs whose diet was supplemented with oleic acid, as expected.

Increased pork belly firmness is a desirable trait, since in general the firmer the pork belly the more readily processible it is. Pork belly firmness is a function of iodine value and generally increases, along with oxidative stability, as iodine value decreases. As shown in Table 4, iodine values trended lower in the belly adipose tissue from pigs whose diet was supplemented with oleic acid. This positive result is consistent with the results in Table 3 above, which showed that the lateral flex score—a measure of firmness—increased when the level of oleic acid in the feed was increased.

The data in Table 4 was recalculated in terms of oleic acid level and tocotrienol addition. The results are given in Table 5 below:

TABLE 5

EFFECT OF OLEIC ACID LEVEL AND DIETARY
TOCOTRIENOL SUPPLEMENTATION ON BELLY
ADIPOSE TISSUE FATTY ACID COMPOSTION[1]

| Item | Oleic Acid Level | | Tocotrienol Addition | |
|---|---|---|---|---|
| | Normal | High | 0 ppm | 225 ppm |
| Monounsaturated Fatty Acid (MUFA) | 42.12[a] | 55.55[b] | 48.76 | 48.91 |
| Polyunsaturated Fatty Acids (PUFA) | 20.54[a] | 9.67[b] | 14.90 | 15.31 |
| Iodine Value (IV) | 70.0[a] | 63.7[b] | 66.4 | 67.3 |

[1]Treatment means in same Oleic Acid Level row with unlike superscripts differ (P < or = 0.05).

As indicated in Table 5, the MUFA increase and PUFA decrease shown in Table 4 in the HO+TT diet compared to the normal (CO) diet was due to the increased level of oleic acid in the feed, not the additional tocotrienols. Likewise, Table 5 indicates that the decrease in iodine value shown in Table 4 in the (HO+TT) diet compared to the normal (CO) diet was due to the increased level of oleic acid in the feed, not the additional tocotrienols.

Samples of ground pork were packaged in PVC wrap and kept on simulated retail display for seven days. During that time trained panelists made a subjective determination of the overall color score and percent discoloration of the ground pork.

Overall color was graded on a scale of 1.0 to 5.0 as follows: 1.0=bright grayish-pink or reddish-pink (acceptable), 2.0=grayish-pink or reddish-pink (acceptable), 3.0=slightly dark pink/red/pink/tan(acceptable), 3.5=threshold of retail acceptability, 4.0=moderately tan/pinkish-red (unacceptable), and 5.0=dark tan or dark pinkish-red (unacceptable). The color score values are shown in Table 6 below:

TABLE 6

EFFECT OF FEED SUPPLEMENTS ON
GROUND PORK VISUAL COLOR SCORE[1]

| | Control (Corn oil) CO | Corn oil + 225 ppm TT TT | High oleic sunflower oil HO | High oleic sunflower oil + 225 ppm TT HO + TT |
|---|---|---|---|---|
| Day 1 | 1.79[a] | 1.22[b] | 1.37[b] | 1.39[b] |
| Day 2 | 1.88 | 1.46 | 1.58 | 1.58 |
| Day 3 | 2.22 | 1.41 | 2.00 | 1.63 |
| Day 4 | 3.03 | 2.19 | 2.78 | 2.56 |
| Day 5 | 4.53 | 4.22 | 4.59 | 4.16 |
| Day 6 | 5.00 | 4.44 | 4.63 | 4.44 |
| Day 7 | 5.00 | 5.00 | 5.00 | 4.88 |

[1]Treatment means in same row with unlike superscripts differ (P < or = 0.05).

Referring to Table 6, the visual color scores were consistently improved (i.e. lower values) during all days for the ground pork from pigs whose feed was supplemented with oleic acid and tocotrienols (HO+TT) compared to the control group (CO). For example, at Day 1 the color score was 1.39 for pigs fed the (HO+TT) diet compared to 1.79 for the control group, indicating improved color in the (HO+TT) group. Supplementing the feed with TT also resulted in lower (improved) color scores on Days 1-6, while supplementing the feed with HO resulted in lower color scores on Days 1-4 and 6.

The data in Table 6 for days 3, 4 and 5 was recalculated in terms of oleic acid level and tocotrienol addition. The results are given in Table 7 below:

TABLE 7

EFFECT OF OLEIC ACID LEVEL AND DIETARY
TOCOTRIENOL SUPPLEMENTATION ON GROUND
PORK VISUAL COLOR SCORE[1]

| Item | Oleic Acid Level | | Tocotrienol Addition | |
|---|---|---|---|---|
| | Normal | High | 0 ppm | 225 ppm |
| Day 3 | 1.81 | 1.81 | 2.11[a] | 1.52[b] |
| Day 4 | 2.61 | 2.67 | 2.91 | 2.38 |
| Day 5 | 4.38 | 4.38 | 4.56 | 4.19 |

[1]Treatment means in same Oleic Acid Level row with unlike superscripts differ (P < or = 0.05).

As indicated in Table 7, the improvement (decrease) in color score shown in Table 6 in the (HO+TT) diet compared to the normal (CO) diet was due to the additional tocotrienols, not the increased level of oleic acid in the feed.

Percent discoloration was also determined subjectively. In the table that follows, a higher number indicates a greater percent discoloration:

TABLE 8

EFFECT OF FEED SUPPLEMENTS ON
GROUND PORK DISCOLORATION[1,2]

| | Control (Corn oil) CO | Corn oil + 225 ppm TT TT | High oleic sunflower oil HO | High oleic sunflower oil + 225 ppm TT HO + TT |
|---|---|---|---|---|
| Day 1 | 1.11 | 1.09 | 1.17 | 1.03 |
| Day 2 | 1.33 | 1.17 | 1.29 | 1.17 |
| Day 3 | 2.44 | 1.69 | 2.69 | 2.13 |
| Day 4 | 3.44[a] | 2.38[b] | 3.00[ab] | 2.69[b] |
| Day 5 | 4.50 | 4.06 | 4.78 | 4.50 |
| Day 6 | 5.75 | 4.63 | 5.38 | 4.88 |
| Day 7 | 7.00 | 7.00 | 7.00 | 6.88 |

[1]Treatment means in same row with unlike superscripts differ (P < or = 0.05).
[2]1 = 0% discoloration, 2 = 1-10%, 3 = 11-20%, 4 = 21-50%, 5 = 51-75%, 6 = 76-99%, 7 = 100%

Referring to Table 8, at Days 2, 3, 4, 5 and 6 the percent discoloration was lowest (numerical value was the lowest) for ground pork from pigs whose feed was supplemented with tocotrienols only. For example, at Day 4 the numerical value for pigs fed (TT) was 2.38 (1-10% discoloration), versus 3.44 (11-20% discoloration) for the control group and 2.69 (1-10% discoloration) for the group fed the (HO+TT) diet.

The data in Table 8 for days 3, 4 and 5 was recalculated in terms of oleic acid level and tocotrienol addition. The results are given in Table 9 below:

TABLE 9

EFFECT OF OLEIC ACID LEVEL AND DIETARY TOCOTRIENOL SUPPLEMENTATION ON GROUND PORK DISCOLORATION[1]

| | Oleic Acid level | | Tocotrienol Addition | |
|---|---|---|---|---|
| Item | Normal | High | 0 ppm | 225 ppm |
| Day 3 | 2.06 | 2.41 | 2.56[a] | 1.91[b] |
| Day 4 | 2.91 | 2.84 | 3.22[a] | 2.53[b] |
| Day 5 | 4.28 | 4.64 | 4.64 | 4.28 |

[1]Treatment means in same row with unlike superscripts differ (P < or = 0.05).

As indicated in Table 9, the decrease in ground pork discoloration (indicative of increased shelf life) shown in Table 8 in the HO+TT diet compared to the normal (CO) diet was due to the additional tocotrienols, not the increased level of oleic acid in the feed.

On each of days 1, 4 and 7, post-grinding, one of the trays of uncooked ground pork was opened and a sample submitted for TBARS (thiobarbituric acid reactive substances) determination, a measure of the extent of oxidation. Cooked ground pork was measured for TBARS concentration at 0 hours and 24 hours after cooking. The results are given in Table 10 below.

TABLE 10

COMPARISON OF TBARS CONTENT OF GROUND PORK FOR CONTROL (CO), ADDED TOCOTRIENOLS (TT), HIGH OLEIC (HO) AND HIGH OLEIC - ADDED TOCOTRIENOL (HO + TT) GROUPS[1]

| | CO | TT | HO | HO + TT |
|---|---|---|---|---|
| Uncooked (mg malonaldehyde[2]/kg sample) | | | | |
| Day 1 | 0.30 | 0.31 | 0.28 | 0.27 |
| Day 4 | 0.36 | 0.41 | 0.35 | 0.34 |
| Day 7 | 0.45 | 0.47 | 0.46 | 0.37 |
| Cooked (mg malonaldehyde[2]/kg sample) | | | | |
| 0 hours | 1.17[a] | 0.90[b] | 0.80[b] | 0.58[c] |
| 24 hours | 2.91[a] | 2.25[b] | 1.98[c] | 1.48[d] |

[1]Means within a row with unlike superscripts differ (P < or = 0.05).
[2]Malonaldehyde is a TBARS analyte.

From Table 10 it can be seen that TBARS concentrations of uncooked ground pork were not significantly different between the control, (TT), (HO) or (HO+TT) groups on any day of analysis. However, cooked samples differed between treatments at both 0 hours and 24 hours. Cooked ground pork from the pigs fed the control diet had the highest TBARS concentration of all dietary treatments at both 0 and 24 hours. Adding oleic acid and 225 ppm TT to the dietary feed (the HO+TT group) significantly lowered oxidation as measured by TBARS concentration in the cooked ground pork at 0 hours and 24 hours compared to the TBARS concentration of the control (CO) group. These results indicate that supplementation of swine diet with oleic acid and tocotrienols lowers oxidation in cooked ground pork, thus improving its quality.

The data in Table 10 was recalculated in terms of oleic acid level and tocotrienol addition. The results are given in Table 11 below:

TABLE 11

EFFECT OF OLEIC ACID LEVEL AND DIETARY TOCOTRIENOL SUPPLEMENTATION ON GROUND PORK OXIDATION[1,2]

| | Oleic Acid level | | Tocotrienol Addition | |
|---|---|---|---|---|
| Item | Normal | High | 0 ppm | 225 ppm |
| Uncooked (mg malonaldehyde[2]/kg sample) | | | | |
| Day 0 | 0.30 | 0.28 | 0.29 | 0.29 |
| Day 4 | 0.39 | 0.34 | 0.35 | 0.38 |
| Day 7 | 0.47 | 0.41 | 0.45 | 0.42 |
| Cooked (mg malonaldehyde[2]/kg sample) | | | | |
| 0 hours | 1.04[a] | 0.69[b] | 0.98[a] | 0.74[b] |
| 24 hours | 2.58[a] | 1.73[b] | 2.45[a] | 1.86[b] |

[1]Treatment means in same row with unlike superscripts differ (P < or = .05).
[2]Malonaldehyde is a TBARS analyte.

As indicated in Table 11, the decrease in TBARS concentration (indicative of lower oxidation) shown in Table 9 for swine fed the (HO+TT) diet compared to the normal (CO) diet was due to both the higher oleic acid level in the feed and the additional tocotrienols.

EXAMPLE 2

Demonstration that In Vitro Addition of Gamma-Tocopherol to High-Oleic Acid Ground Pork Results in Improved Oxidative Stability Applicants assessed the effects of in vitro addition of gamma-tocopherol to ground pork from swine fed a diet supplemented with oleic acid in order to evaluate gamma tocopherol's value as an animal feed supplement when used in conjunction with oleic acid. Gamma-tocopherol was added to the raw (uncooked) ground pork from swine whose diet was not supplemented with oleic acid and swine whose diet was supplemented with oleic acid. Ground pork from pigs fed the respective treatments were formed into patties, cooked and refrigerated for two days in plastic pouches. Samples of the cooked patties were then submitted for TBARS (thiobarbituric acid reactive substances) determination at 0 hours and 24 hours following refrigeration. The results are given in Table 12 below.

TABLE 12

COMPARISON OF TBARS CONTENT OF COOKED GROUND PORK PATTIES WITH AND WITHOUT SUPPLEMENTED GAMMA-TOCOPHEROL
mg malonaldehyde[5]/kg sample

| | CO[1] | 100 ppm GT[2] | HO[3] | (HO + GT)[4] |
|---|---|---|---|---|
| 0 hours | 1.53 | 0.746 | 1.37 | 0.567 |
| 24 hours | 2.14 | 1.24 | 1.85 | 0.95 |

[1]CO = Cooked ground pork from swine fed control diet. No added GT.
[2]100 ppm GT = Cooked ground pork from swine fed control diet, 100 ppm GT added in vitro to raw ground pork.
[3]HO = Cooked ground pork from swine fed high oleic diet. No added GT.
[4]HO + GT = Cooked ground pork from swine fed high oleic diet, GT added in vitro.
[5]Malonaldehyde is a TBARS analyte.

From Table 12 it can be seen that cooked ground pork from the pigs fed the control diet and which had no added GT (the CO data) had the highest TBARS concentration of all dietary treatments at both 0 and 24 hours after refrigeration. Adding 100 ppm GT to the ground pork from swine fed the high-oleic diet (the HO+GT data) resulted in the lowest TBARS concentrations of the four groups. These results suggest that supplementation of swine diet with oleic acid and gamma-tocopherol will lower oxidation in cooked ground pork, thus improving its quality.

Examples 1 and 2 demonstrate that supplementation of swine diet with oleic acid and selected tocols (one or more tocotrienols and/or gamma tocopherol) results in improved meat quality as measured by pork belly lateral flex score (Tables 2 and 3), fatty acid profile and iodine value (Tables 4 and 5), color (Tables 6, 7, 8 and 9) and cooked meat oxidative stability (Tables 10 and 11). In particular, pigs fed oleic acid tended to have higher pork belly lateral flex scores (Table 3), increased MUFA concentrations and lower iodine values (Table 5), and lowered TBARS concentration in the cooked meat (Table 11), while pigs fed 225 ppm tocotrienols in their diet tended to have improved color stability (Tables 7 and 9) and lowered TBARS concentration in the cooked meat (Table 11). Most significantly, it was demonstrated that adding both oleic acid and tocotrienols had a greater effect on lowering cooked pork TBARS concentration than adding just oleic acid or just tocotrienols (Table 10). It was also demonstrated that adding both oleic acid and (in vitro) gamma-tocopherol had a greater effect on lowering cooked ground pork TBARS concentration than adding just oleic acid or just gamma-tocopherol (Table 12). The improvements have been demonstrated on swine, and are expected to occur in other non-ruminants.

EXAMPLE 3

2004 Cattle Feed Test

Demonstration that Supplementation of Cattle Diet with Oleic Acid and Tocotrienols Results in Improved Tissue Quality Parameters Applicants assessed the effects of supplementing the animal diet with oleic acid and tocotrienol on beef quality in an experiment in which data from steers fed one of four dietary treatments were compared. The steers were blocked by weight (heavy or light) and assigned to eight outdoor group pens with five steers per pen. Pens were randomly assigned within each of the two weight blocks to four dietary treatments: (1) simulated oil-rich corn grain (coarse corn grits with corn oil added as 6% of the weight of the grits plus oil) (CO); (2) simulated oil-rich corn grain (coarse corn grits with a similar level of corn oil) with supplemental tocotrienol (CO+TT), (3) simulated high oleic acid corn grain (coarse corn grits with high oleic sunflower oil added as 6% of the weight of the grits plus oil) (HO); and (4) simulated high oleic acid corn grain (coarse corn grits with high oleic sunflower oil added as 6% of the weight of the grits plus oil) with supplemental tocotrienol (HO+TT); as summarized below:

TABLE 13

DIETARY TREATMENTS

| Treatment | Total Dietary Oil Content, % | Oleic acid content of oil | | Tocotrienol, ppm[1] |
|---|---|---|---|---|
| | | Corn Oil | Sunflower Oil | |
| 1 Normal oleic acid (CO) | 6 | 29.6% | | 0 |
| 2 Normal oleic acid + TT (CO + TT) | 6 | 29.6% | | 150 |
| 3 Simulated high oleic acid (HO) | 6 | | 80.2% | 0 |
| 4 Simulated high oleic acid + TT (HO + TT) | 6 | | 80.2% | 150 |

[1]The 150 ppm dietary treatment included about 50 ppm alpha-tocopherol, for a total tocol concentration of about 200 ppm.

In the normal or control (CO) diet, the total dietary content of oil was 6 wt % of the feed. The oil was a typical corn oil having an oleic acid content of about 29.6% of the fatty acid fraction. In the simulated high-oleic acid (HO) diet, the total dietary content of oil was still 6 wt %, but the oil was high-oleic sunflower oil with an oleic acid content of about 80.2% of the fatty acid fraction. All four experimental diets were formulated with coarse corn grits.

The steers were fed their respective dietary supplements for 133 days starting Apr. 12, 2004 and ending Aug. 23, 2004. The cattle were loaded on Aug. 24, 2004 and transported to Emporia, Kans. for harvest at the IBP packing plant. Steaks and ground beef samples were evaluated for, among other things, color, shelf life (as measured by percent discoloration over time) and rancidity (as measured by TBARS concentration over time).

Ribeye steaks utilized for color evaluation were placed onto 17S foam trays with meat, fish and poultry pads (Dri-Loc AC-50) and wrapped with polyvinyl chloride (PVC) film. The steaks were placed under simulated retail display at 34+/−3 degree F. in open top cases programmed to defrost twice daily for seven days. During that time trained panelists made subjective determinations of the overall color score and percent discoloration of the ribeye steaks. Overall color was graded on a scale of 1.0 to 5.0 as follows: 1.0=Very bright red; 2.0=Bright cherry red; 3.0=Slightly dark red to tannish red; 4.0=Moderately dark red to brown; 5.0=Very dark red/purple to brown. The color score values are shown in Table 14 below:

TABLE 14

EFFECT OF FEED SUPPLEMENTS ON UNCOOKED RIBEYE STEAK VISUAL COLOR SCORE[1]

| | Control (Corn oil) CO | Corn oil + 150 ppm TT CO + TT | High oleic Sunflower oil HO | High oleic sunflower oil + 150 ppm TT HO + TT |
|---|---|---|---|---|
| Day 1 | 2.2 | 2.3 | 2.3 | 2.3 |
| Day 2 | 2.6 | 2.5 | 2.7 | 2.5 |
| Day 3 | 2.9 | 2.6 | 2.7 | 2.6 |
| Day 4 | 3.0 | 2.8 | 2.7 | 2.6 |
| Day 5 | 3.2 | 2.8 | 2.8 | 2.7 |
| Day 6 | 3.3 | 3.0 | 2.9 | 2.7 |
| Day 7 | 3.7$^a$ | 3.1$^b$ | 3.0$^{bc}$ | 2.9$^c$ |

[1]Treatment means in same row with unlike superscripts differ (P < or = 0.05).

Referring to Table 14, dietary treatment affected visual color scores to a statistically significant extent on only Day 7. However, the color scores did trend lower (indicating better quality) for most days when either tocotrienols (CO+TT), oleic acid (HO) or both oleic acid and tocotrienols (HO+TT) were added to the diet. Color scores were greater (less desirable) for steaks from steers fed the control (CO) diet than any other diet. Steaks from steers fed the CO+TT diet had higher (less desirable) color scores than steaks from steers fed the HO+TT diet on days 4-7 suggesting that adding both oleic acid and tocotrienols is better than adding only tocotrienols to the diet.

The data in Table 14 for days 1, 3 and 7 was recalculated in terms of oleic acid level and tocotrienol addition. The results are presented in Table 15 below:

TABLE 15

EFFECT OF FEED SUPPLEMENTS ON UNCOOKED RIBEYE STEAK VISUAL COLOR SCORE[1]

| | Oil Source | | Tocotrienol Addition | |
|---|---|---|---|---|
| | Corn oil | Sunflower oil | 0 ppm | 150 ppm |
| Day 3 | 2.7 | 2.6 | 2.8$^a$ | 2.6$^b$ |
| Day 5 | 3.0$^a$ | 2.7$^b$ | 3.0$^a$ | 2.8$^b$ |
| Day 7 | 3.4 | 3.0 | 3.4 | 3.0 |

[1]Treatment means in same Oleic Acid Level row with unlike superscripts differ (P < or = 0.05).

As indicated in Table 15, visual color scores of uncooked ribeye steaks on days 3, 5 and 7 decreased when either oleic acid (in the form of sunflower oil) or tocotrienols were added to the feed.

Percent discoloration was also determined subjectively. In the table that follows, a higher number indicates a greater percent discoloration:

TABLE 16

EFFECT OF FEED SUPPLEMENTS ON UNCOOKED RIBEYE STEAK DISCOLORATION[1,2]

| | Control (Corn oil) CO | Corn oil + 150 ppm TT CO+TT | High oleic sunflower oil HO | High oleic sunflower oil + 150 ppm TT HO + TT |
|---|---|---|---|---|
| Day 1 | 1.0 | 1.1 | 1.1 | 1.1 |
| Day 2 | 1.1 | 1.0 | 1.0 | 1.0 |
| Day 3 | 1.5 | 1.4 | 1.4 | 1.4 |
| Day 4 | 1.1 | 1.0 | 1.0 | 1.1 |
| Day 5 | 1.4 | 1.1 | 1.1 | 1.1 |
| Day 6 | 2.2$^a$ | 1.3$^b$ | 1.3$^b$ | 1.3$^b$ |
| Day 7 | 3.4$^a$ | 1.8$^b$ | 1.6$^b$ | 1.6$^b$ |

[1]Treatment means in same row with unlike superscripts differ (P < or = 0.05).
[2]1.0 = No discoloration, 2.0 = Slight discoloration (1-10%), 3 = Small discoloration (11-25%), 4 = Modest discoloration (26-50%), 5 = Moderate discoloration (51-75%), 6 = Extensive discoloration (76-99%), 7 = 100% discoloration.

Referring to Table 16, on days 6 and 7 the discoloration was lowest (numerical value was the lowest) for uncooked ribeye steaks from steers whose feed was supplemented with either oleic acid (in the form of high oleic sunflower oil instead of corn oil), tocotrienols, or both oleic acid and tocotrienols. Furthermore, these lower percent discoloration numbers observed on days 6 and 7 were statistically significant.

The data in Table 16 for days 1, 3 and 7 were recalculated in terms of oleic acid level and tocotrienol addition. The results are given in Table 17 below:

TABLE 17

EFFECT OF FEED SUPPLEMENTS ON UNCOOKED RIBEYE STEAK DISCOLORATION[1]

| | Oleic Acid level | | Tocotrienol Addition | |
|---|---|---|---|---|
| | Normal | High | 0 ppm | 150 ppm |
| Day 3 | 1.5 | 1.4 | 1.4 | 1.4 |
| Day 5 | 1.3$^a$ | 1.1$^b$ | 1.2$^a$ | 1.1$^b$ |
| Day 7 | 2.6 | 1.6 | 2.5 | 1.7 |

[1]Treatment means in same row with unlike superscripts differ (P < or = 0.05).

As indicated in Table 17, uncooked ribeye steaks from steers fed either the high oleic acid diet and the added tocotrienol diet exhibited less discoloration than the uncooked ribeye steaks from steers fed the normal (control) diet. This indicates that the decrease in uncooked ribeye steak discoloration (indicative of increased shelf life) shown in Table 16 for the HO+TT diet compared to the normal (CO) diet appears to be due to the addition of both oleic acid and tocotrienols.

Results from Hunter Lab* instrumental color evaluation of ribeye steaks are presented in Tables 18 and 19.

TABLE 18

EFFECT OF FEED SUPPLEMENTS ON RIBEYE STEAK HUNTER a* COLOR SCORE[1]

| | Control (Corn oil) CO | Corn oil + 150 ppm TT CO+TT | High oleic sunflower oil HO | High oleic sunflower oil + 150 ppm TT HO + TT |
|---|---|---|---|---|
| Day 1 | 33.33 | 33.15 | 33.38 | 33.68 |
| Day 2 | 32.88 | 32.89 | 33.18 | 33.16 |
| Day 3 | 32.48 | 32.91 | 33.23 | 33.24 |
| Day 4 | 31.62 | 32.72 | 32.87 | 33.14 |
| Day 5 | 30.19$^b$ | 32.32$^a$ | 32.76$^a$ | 32.93$^a$ |
| Day 6 | 28.45$^b$ | 31.73$^a$ | 32.10$^a$ | 32.34$^a$ |
| Day 7 | 27.21$^b$ | 31.05$^a$ | 31.72$^a$ | 32.37$^a$ |

[1]Treatment means in same row with unlike superscripts differ (P < or = 0.05).

Higher Hunter a* values are associated with a greater degree of "redness" in fresh beef samples, which is desired by consumers. Referring to Table 18, dietary treatment effects became apparent on Day 5, with ribeye steaks from the feed supplement groups (TT, HO and HO+TT) having higher (P< or =0.05) Hunter a* values than steaks from the control (CO) group. These differences continued through Day 7.

The data in Table 18 was recalculated in terms of oleic acid level and tocotrienol addition. The results are given in Table 19 below:

TABLE 19

EFFECT OF FEED SUPPLEMENTATION ON RIBEYE STEAK HUNTER a* COLOR SCORE[1]

| | Oil Source | | Tocotrienol Addition | |
|---|---|---|---|---|
| | Corn oil | Sunflower oil | 0 ppm | 150 ppm |
| Day 1 | 33.24 | 33.53 | 33.35 | 33.42 |
| Day 2 | 32.88 | 33.17 | 33.03 | 33.02 |
| Day 3 | 32.70 | 33.24 | 32.86 | 33.08 |
| Day 4 | 32.17$^a$ | 33.00$^b$ | 32.24 | 32.93 |
| Day 5 | 31.25 | 32.84 | 31.47 | 32.63 |

TABLE 19-continued

EFFECT OF FEED SUPPLEMENTATION ON RIBEYE STEAK HUNTER a* COLOR SCORE[1]

|  | Oil Source | | Tocotrienol Addition | |
|---|---|---|---|---|
|  | Corn oil | Sunflower oil | 0 ppm | 150 ppm |
| Day 6 | 30.09 | 32.22 | 30.27 | 32.03 |
| Day 7 | 29.13 | 32.04 | 29.46 | 31.71 |

[1]Treatment means in same Oleic Acid Level row with unlike superscripts differ (P < or = 0.05).

As indicated in Table 19, oil source influenced Hunter a* values on Day 4 only. Tocotrienol addition did not significantly effect Hunter a* on any day. However, both oleic acid and tocotrienol addition resulted in directional improvements (increasing) in Hunter a* values on most days.

Uncooked and cooked ribeye steak samples were evaluated for TBARS (thiobarbituric acid reactive substances), a measure of the extent of oxidation. The uncooked ribeye steaks were measured for TBARS concentration pre-, mid- and post-display. The cooked steaks were cooked in a Blodgett oven set at 163 degrees Centigrade. The steaks were turned when their internal temperature reached 40 degrees C., removed from the oven at 70 degrees C. and allowed to temper for handling. The cooked steaks were covered with plastic wrap and refrigerated at approximately 3-4 degrees C. for 24 hours. The steaks were then thawed and cut samples were vacuum-packaged for TBARS analysis.

The steaks for warmed-over TBARS analysis were cooked as described above, wrapped in aluminum foil and refrigerated at 3-4 degrees C. for 44 to 48 hours prior to reheating. They were reheated to 66 degrees C., then vacuum packaged for TBARS analysis. The uncooked and cooked ribeye steak results are given in Table 20 below:

TABLE 20

COMPARISON OF TBARS CONTENT OF UNCOOKED AND COOKED RIBEYE STEAKS[1]

|  | CO | TT | HO | HO + TT |
|---|---|---|---|---|
| Uncooked (mg malonaldehyde[2]/kg sample) | | | | |
| Pre-display | 0.16$^a$ | 0.09$^{bc}$ | 0.11$^b$ | 0.08$^c$ |
| Mid-display[3] | 0.44$^a$ | 0.09$^b$ | 0.11$^b$ | 0.05$^b$ |
| Post-display | 1.40$^a$ | 0.20$^b$ | 0.22$^b$ | 0.19$^b$ |
| Cooked (mg malonaldehyde[2]/kg sample) | | | | |
| Freshly cooked | 0.51 | 0.45 | 0.46 | 0.46 |
| Warmed-over | 1.04 | 0.71 | 0.91 | 0.68 |

[1]Means within a row with unlike superscripts differ (P < or = 0.05).
[2]Malonaldehyde is a TBARS analyte.
[3]Mid-display time point was 3½ days; post-display time point was 7 days.

From Table 20 it can be seen that TBARS concentrations of uncooked ribeye steaks were significantly lower (P< or = 0.05) at pre-, mid- and post-display time points in the steak samples from steers fed the high oleic-added tocotrienol (HO+TT) diet compared to the normal (CO) diet. The TBARS concentrations of cooked samples were not different at P< or =0.05, although there were directional improvements with all three dietary treatments. These results indicate that supplementation of cattle diet with both a high oleic acid oil such as, but not limited to, sunflower oil and added tocotrienols lowers oxidation in uncooked ribeye steaks and also probably in cooked ribeye steaks, thus improving its quality.

The data in Table 20 was recalculated in terms of oleic acid level and tocotrienol addition. The results are given in Table 21 below:

TABLE 21

EFFECT OF OLEIC ACID LEVEL AND DIETARY TOCOTRIENOL SUPPLEMENTATION ON UNCOOKED AND COOKED RIBEYE STEAK OXIDATION[1,2]

|  | Oil Source | | Tocotrienol Addition | |
|---|---|---|---|---|
|  | Corn oil | Sunflower oil | 0 ppm | 150 ppm |
| Uncooked (mg malonaldehyde[2]/kg sample) | | | | |
| Pre-display | 0.13 | 0.09 | 0.14 | 0.08 |
| Mid-display[3] | 0.26 | 0.08 | 0.28 | 0.07 |
| Post-display | 0.80 | 0.20 | 0.81 | 0.19 |
| Cooked (mg malonaldehyde[2]/kg sample) | | | | |
| Freshly cooked | 0.48 | 0.46 | 0.48 | 0.45 |
| Warmed-over | 0.88 | 0.79 | 0.98$^a$ | 0.69$^b$ |

[1]Treatment means in same row with unlike superscripts differ (P < or = .05).
[2]Malonaldehyde is a TBARS analyte.
[3]Mid-display time point was 3½ days; post-display time point was 7 days.

As indicated in Table 21, both oil source and tocotrienol addition show a directional improvement (lowering) of the TBARS concentration for uncooked and cooked ribeye steaks. The addition of 150 ppm tocotrienols resulted in a significantly lower (P< or =0.05) warmed-over TBARS concentration compared to the 0 ppm tocotrienols diet. It can be concluded that the decrease in TBARS concentration (indicative of lower oxidation) shown in Table 20 for uncooked and cooked ribeye steaks from steers fed the (HO+TT) diet compared to the normal (CO) diet was probably due to both the higher oleic acid level in the sunflower oil and the additional tocotrienols.

Uncooked and cooked ground beef samples were also analyzed for TBARS concentration to determine if oleic acid and tocotrienols were effective in improving oxidative stability (lowering TBARS concentration) in ground beef. The effects of dietary treatment were observed in uncooked ground beef pre-display, mid-display and post-display. The effects of dietary treatment were observed in freshly cooked ground beef and warmed-over ground beef. The results are given in Table 22 below:

TABLE 22

COMPARISON OF TBARS CONTENT IN UNCOOKED AND COOKED GROUND BEEF[1]

|  | CO | TT | HO | HO + TT |
|---|---|---|---|---|
| Uncooked (mg malonaldehyde[2]/kg sample) | | | | |
| Pre-display | 0.48 | 0.27 | 0.37 | 0.12 |
| Mid-display | 1.18$^a$ | 0.38$^{bc}$ | 0.52$^b$ | 0.18$^c$ |
| Post-display | 2.18$^a$ | 0.53$^b$ | 0.54$^b$ | 0.24$^b$ |
| Cooked (mg malonaldehyde[2]/kg sample) | | | | |
| Freshly cooked | 1.02 | 0.72 | 0.78 | 0.64 |
| Warmed-Over | 1.83 | 1.21 | 1.33 | 1.15 |

[1]Means within a row with unlike superscripts differ (P < or = 0.05).
[2]Malonaldehyde is a TBARS analyte.
[3]Mid-display time point was 2½ days; post-display time point was 5 days.

From Table 22 it can be seen that TBARS concentrations were significantly lower (P< or =0.05) at mid-display and post-display for uncooked ground beef from steers fed the high oleic acid (sunflower oil) diet (HO), the added tocotrienol diet (TT) and the high oleic acid and added tocotrienol diet (HO+TT) compared to the uncooked ground beef from steers fed the control (CO) diet. The greatest improvement in TBARS (lowest TBARS concentration) was observed in the uncooked ground beef from the steers fed the (HO+TT) diet, indicating that there is an additive effect when supplementing cattle feedstock with both oleic acid and tocotrienols.

TBARS concentrations in freshly cooked and warmed-over ground beef were not significantly different between the four dietary treatments: (CO), (TT), (HO) or (HO+TT). However, directional improvements over the control (CO) group were seen for all three other dietary treatments, with the greatest improvement being in the ground beef from steers fed sunflower oil and 150 ppm added tocotrienol (HO+TT).

These results suggest that supplementation of cattle diet with oleic acid and tocotrienols lowers oxidation in uncooked and cooked ground beef, thus improving its quality.

The data in Table 22 was recalculated in terms of oleic acid level and tocotrienol addition. The results are given in Table 23 below:

TABLE 23

EFFECT OF OIL SOURCE AND DIETARY TOCOTRIENOL SUPPLEMENTATION ON UNCOOKED AND COOKED GROUND BEEF OXIDATION[1]

| | Oil Source | | Tocotrienol Addition | |
|---|---|---|---|---|
| | Corn oil | Sunflower oil | 0 ppm | 150 ppm |
| Uncooked (mg malonaldehyde[2]/kg sample) | | | | |
| Pre-display | 0.38 | 0.24 | $0.43^a$ | $0.19^b$ |
| Mid-display | 0.78 | 0.35 | 0.85 | 0.28 |
| Post-display | 1.35 | 0.39 | 1.36 | 0.39 |
| Cooked (mg malonaldehyde[2]/kg sample) | | | | |
| Freshly cooked | $0.71^a$ | $0.59^b$ | $0.73^a$ | $0.56^b$ |
| Warmed over | $1.25^a$ | $1.02^b$ | $1.30^a$ | $0.97^b$ |

[1]Treatment means in same row with unlike superscripts differ (P < or = .05).
[2]Malonaldehyde is a TBARS analyte.

As indicated in Table 23, TBARS concentration in the uncooked ground beef was directionally lower for the sunflower oil compared to the corn oil. TBARS concentration was significantly (P< or =0.05) lower pre-display for the 150 ppm added tocotrienol diet compared to the 0 ppm added tocotrienol diet (0.19 mg/kg versus 0.43 mg/kg). TBARS concentration in the freshly cooked and warmed-over ground beef was significantly lower (P< or =0.05) for the sunflower oil compared to the corn oil and for the 150 ppm added tocotrienols compared to the 0 ppm tocotrienols. These results suggest that the decrease in TBARS concentration shown in Table 22 for uncooked and cooked ground beef from steers fed the (HO+TT) diet compared to the normal (CO) diet was due to both the oil source (sunflower oil) in the feed and the additional tocotrienols.

Results of TBARS assays in cooked fajitas are presented in Tables 24 and 25. The fajitas were prepared as follows. Frozen raw material was tempered to 32-34 degrees C. All silver skin that was not transparent was removed and surface fat was removed to the size of 1 inch diameter and less than ¼ inch thick. Skirt steaks were cut into two or three pieces and placed with marinade ingredients into a tumbler. A vacuum was drawn and steaks were tumbled for 45 minutes, and then held for twelve hours until cooking. Meat was cooked to an internal temperature of about 170 degrees F. and run through a slicer. Slices were then used in the preparation of cooked fajitas. Results of TBARS assays in the cooked fajitas are presented in Table 24 below:

TABLE 24

COMPARISON OF TBARS CONTENT OF COOKED FAJITAS[1]

| | CO | TT | HO | HO + TT |
|---|---|---|---|---|
| | (mg malonaldehyde[2]/kg sample) | | | |
| Day 0 | $1.08^a$ | $0.54^b$ | $0.50^b$ | $0.48^b$ |
| Day 7 | $9.04^a$ | $1.13^{bc}$ | $1.31^{bc}$ | $0.51^c$ |
| Day 14 | 8.29 | 1.54 | 1.77 | 0.74 |
| Day 16 | $11.3^a$ | $1.05^b$ | $0.73^b$ | $1.03^b$ |
| Day 21 | $10.5^a$ | $1.34^b$ | $6.02^b$ | $1.54^c$ |
| Day 28 | $10.8^a$ | $11.3^a$ | $5.05^{bc}$ | $0.90^c$ |

[1]Means within a row with unlike superscripts differ (P < or = 0.05).
[2]Malonaldehyde is a TBARS analyte.

From Table 24 it can be seen that treatment effects (P< or = 0.05) were noted for all days except day 14. Overall, TBARS concentrations were lowest (indicating the best result) in the fajitas from the (HO+TT) group and highest in fajitas from the control (CO) group. These results indicate that supplementation of cattle diet with both a high oleic acid oil like sunflower oil and added tocotrienols lowers oxidation in cooked fajitas, thus improving their quality.

The data in Table 24 were recalculated in terms of oleic acid level and tocotrienol addition. The results are given in Table 25 below:

TABLE 25

EFFECT OF OLEIC ACID LEVEL AND DIETARY TOCOTRIENOL SUPPLEMENTATION ON COOKED FAJITAS OXIDATION[1,2]

| | Oil Source | | Tocotrienol Addition | |
|---|---|---|---|---|
| | Corn oil | Sunflower oil | 0 ppm | 150 ppm |
| | (mg malonaldehyde[2]/kg sample) | | | |
| Day 0 | $0.81^a$ | $0.49^b$ | $0.79^a$ | $0.51^b$ |
| Day 7 | $5.09^a$ | $0.91^b$ | $5.18^a$ | $0.82^b$ |
| Day 14 | 4.92 | 1.25 | 5.03 | 1.14 |
| Day 16 | $6.17^a$ | $0.88^b$ | $6.00^a$ | $1.04^b$ |
| Day 21 | 5.94 | 3.78 | $8.28^a$ | $1.44^b$ |
| Day 28 | $11.0^a$ | $2.97^b$ | 7.91 | 6.11 |

[1]Treatment means in same row with unlike superscripts differ (P < or = .05).
[2]Malonaldehyde is a TBARS analyte.

As indicated in Table 25, oil source influenced (P< or = 0.05) TBARS concentrations on days 0, 7, 16 and 28, with fajitas prepared from steers fed sunflower oil diets having lower (better) TBARS concentrations than fajitas prepared from steers fed corn oil diets. Feeding added tocotrienol diets resulted in lower (P< or =0.05) TBARS levels on days 0, 7, 16 and 21. Day 14 and day 28 TBARS concentrations were also lower for the added tocotrienol group but the difference was not statistically significant at P< or =0.05. Day 14 and day 21 TBARS concentrations were lower for the sunflower group but those differences were not statistically significant at P< or =0.05. It can be concluded that the decrease in TBARS concentration (indicative of lower oxidation) shown in Table 24 for cooked fajitas from steers fed the (HO+TT) diet compared to the normal (CO) diet was due to both the higher oleic acid level in the sunflower oil and the additional tocotrienols.

Example 3 demonstrates that all three dietary treatments—(1) HO: simulated high oleic acid corn grain, (2) TT: corn grain plus 150 ppm added tocotrienols, and (3) HO+TT: simulated high oleic acid corn grain plus 150 ppm added tocotrienols-exhibited at least directional improvements in meat quality as measured by subjective color in uncooked ribeye steaks (Tables 14 and 15), percent discoloration in uncooked ribeye steaks (Tables 16 and 17), Hunter a* color values in uncooked ribeye steaks (Tables 18 and 19), oxidative stability in uncooked and cooked ribeye steaks (Tables 20 and 21), oxidative stability in uncooked and cooked ground beef (Tables 22 and 23), and oxidative stability in cooked fajitas (Tables 24 and 25).

In particular, ribeye steaks from steers whose feed was supplemented with high oleic acid sunflower oil and 150 ppm tocotrienols tended to have improved (lower) subjective color scores (Table 14), lower percent discoloration (Table 16), better (higher) Hunter a* scores (Table 18) and lower TBARS concentration (Table 20). Ground beef and cooked fajitas from steers whose feed was supplemented with high oleic acid sunflower oil and 150 ppm tocotrienols tended to have lower TBARS concentration (Tables 22 and 24).

It was further demonstrated that in most instances adding both high oleic acid sunflower oil and 150 ppm tocotrienols had a greater effect on lowering TBARS concentration in uncooked and cooked ribeye steaks (Table 20), uncooked and cooked ground beef (Table 22) and cooked fajitas (Table 24) than adding just high oleic acid sunflower oil or just tocotrienols.

The improvements have been demonstrated on steer, and are expected to occur in other ruminants.

EXAMPLE 4

The Effects of High Tocotrienol Maize Grain on Meat Quality

When Fed to Broiler Chicks

Materials and Methods

Newly hatched broilers of a commercial strain were obtained in sufficient numbers to assure availability of 42 healthy chicks. Chicks were evaluated upon receipt for overall health, signs of disease, or other complications that might affect the outcome of the study. Birds were weighed, wing-banded for identification purposes, and randomly placed in three floor pens (14 per pen, 7 males and 7 females) upon receipt (Day 0). Birds were housed in a facility with forced air heaters and heat lamps. A continuous (24 hour) lighting program for broilers was followed.

Pens were randomly assigned to the following dietary treatments: commercial corn-based diet (Pioneer hybrid 3335) without supplemental tocotrienol (Negative Control); commercial corn-based diet supplemented with Tocotab 30 (Positive Control); and corn-based diet formulated with HGGT corn (HGGT, lot # R04CN-YO-48). Tocotab 30 contained 40.6% total tocols by weight. The HGGT grain contained an estimated 292 ppm total tocol, of which an estimated 92.5% (approximately 270 ppm) was tocotrienol (mostly γ-tocotrienol).

Treatment diets were manufactured at the Pioneer Livestock Nutrition Center (Polk City, Iowa). The targeted dietary tocol concentration of the Positive Control and HGGT diets was 180 ppm. A two-phase feeding system was used in this trial: starter (days 0 to 21), and grower/finisher (days 22 to 42). Diets were formulated to meet or exceed minimum amino acid allowances recommended by NRC (1994). All diets were fed in mash form, and diets and water were provided ad libitum. Feed samples of each treatment were collected and submitted for determination of moisture, protein, fat, gross energy, calcium, phosphorus, amino acid profile, and total tocol content. Diets were fed for a total of 42 days; treatments were initiated on Nov. 2, 2004, and terminated on Dec. 14, 2004.

Birds were weighed on days 0, 21 and 42, and feed intakes calculated for the respective feeding periods. Broilers were observed for any changes in health or behavior; no mortalities occurred during the trial. Birds were sacrificed at the end of the 42-day feeding period, and remaining test feeds were disposed of by composting.

Breast and thigh samples were collected at the time of harvest and sent to Pioneer for analysis. Determination of warmed-over flavor as indicated by thiobarbituric reactive substance (TBARS) analysis was performed on freshly cooked and warmed-over (24 hours) breast and thigh samples. Six composite samples were made for each treatment group due to insufficient sample from each bird. Each breast sample composite consisted of samples from three birds, while each thigh sample composite consisted of samples from four birds.

TBARS data were analyzed using the MIXED Procedure of SAS. The pooled sample was considered to be the experimental unit, and the model for data analysis consisted of treatment as a fixed effect.

Results and Discussion

Concentrations of TBARS in freshly cooked and warmed-over (24 hours) breast and thigh meat differed (P 0.05) between treatment groups as shown in Table 26. Values for freshly cooked or warmed-over breast meat were lower (i.e. improved) for birds fed Positive Control or HGGT diets. TBARS concentrations in freshly cooked thigh meat tended (P=0.068) to be lower for the HGGT group as compared to the Negative Control group; Positive Control group values were intermediate. Warmed-over TBARS concentrations were lower (P≤0.05) for the HGGT and Positive Control groups.

TABLE 26

EFFECT OF DIETARY TREATMENT ON TBARS CONCENTRATIONS IN FRESHLY COOKED AND WARMED-OVER (24 HOURS) BREAST AND THIGH MEAT[1]

| Item | Negative Control | Positive Control | HGGT | SEM | P value |
|---|---|---|---|---|---|
| Breast | | | | | |
| Freshly cooked | 1.02a | 0.63b | 0.76b | 0.08 | 0.0131 |
| Warmed-over | 4.76a | 3.47b | 3.68b | 0.33 | 0.0332 |
| Thigh | | | | | |
| Freshly cooked | 2.93 | 2.16 | 1.77 | 0.31 | 0.0680 |
| Warmed-over | 7.58a | 6.32b | 6.24b | 0.22 | 0.0033 |

[1]Treatment means in same row without a common superscript letter differ (P ≤ .05).

Summary

The impact of dietary tocols on meat quality was evaluated in a feeding trial with broilers. Newly hatched male and female broiler chicks of a commercial strain (n=42) were randomly assigned to dietary treatments (14 birds/treatment) that consisted of: diet without supplemental tocols (Negative Control), or diets with tocols from two sources, TocoTab 30 (Positive Control) or HGGT corn. Birds were fed diets for 42 days and breast and thigh samples collected at harvest for TBARS analysis. TBARS values for freshly cooked or warmed-over breast meat were lower (P≤0.05) for birds fed PC or HGGT diets. Warmed-over TBARS concentrations in thigh meat were lower (P≤0.05) for the HGGT and PC treatment groups.

Other modifications and alternative embodiments of the invention are contemplated which do not depart from the scope of the invention as defined by the foregoing teachings and appended claims. It is intended that the claims cover all such modifications that fall within their scope.

What is claimed is:

1. A method of improving the meat tissue quality of a bovine comprising; feeding the bovine a diet comprising between 3% and 8% total dietary oil with oleic acid comprising at least 50% of the fatty acid fraction of the oil and at least 275 ppm tocotrienols, wherein said diet comprises a cereal grain crop or oilseed, wherein said cereal grain crop or said oilseed is modified to have elevated levels of oleic acid and tocotrienols, wherein the quality of the meat is measured by the criteria selected from the group consisting of improved color, decreased fresh meat discoloration and improved oxidative stability.

2. The method of claim 1, wherein oleic acid comprises at least 70% of the fatty acid fraction.

3. The method of claim 1, wherein the bovine is fed the diet over a period of at least 20 days.

4. The method of claim 1, wherein the cereal grain crop is corn.

5. The method of claim 4, wherein the corn comprises both a fatty acid desaturase 2 (FAD2) gene and a homogentisate geranylgeranyl transferase (HGGT) gene for the high-oleic acid and high tocotrienol phenotypes.

6. The method of claim 5, wherein the diet is fed over a period of at least 30 days.

7. The method of claim 1, wherein the diet is fed over a period of at least 50 days.

8. The method of claim 1, wherein the animal is fed the diet for at least 100 days.

9. The method of claim 1, wherein the diet comprises about 5% total dietary oil with oleic acid comprising at least 50% of the fatty acid fraction and at least 275 ppm of tocotrienols.

10. The method of claim 9, wherein oleic acid comprises at least 70% of the fatty acid fraction.

11. The method of claim 1, wherein the diet comprises between 3% and 8% total dietary oil with oleic acid comprising at least 50% of the fatty acid fraction of the oil and between 275 ppm and 500 ppm of tocotrienols.

12. The method of claim 11, wherein the oleic acid comprises at least 80% of the fatty acid fraction of the oil.

13. The method of claim 12, wherein diet comprises between 3% and 8% total dietary oil with oleic acid comprising at least 70% of the fatty acid fraction of the oil and between 275 ppm and 300 ppm of tocotrienols.

14. The method of claim 13, wherein the diet comprises between 5% and 8% total dietary oil with oleic acid comprising at least 70% of the fatty acid fraction of the oil.

* * * * *